United States Patent
Buschmann et al.

(10) Patent No.: US 7,168,937 B2
(45) Date of Patent: Jan. 30, 2007

(54) METHOD FOR THE ENZYMATIC RESOLUTION OF THE RACEMATES OF AMINOMETHYL-ARYL-CYCLOHEXANOL DERIVATIVES

(75) Inventors: Helmut Buschmann, Aachen (DE); Dagmar Kaulartz, Stolberg (DE); Carsten Griebel, Aachen (DE); Hans-Joachim Gais, Aachen (DE)

(73) Assignee: Gruenenthal GmbH, Aachen (DE)

( * ) Notice: Subject to any disclaimer, the term of this patent is extended or adjusted under 35 U.S.C. 154(b) by 417 days.

(21) Appl. No.: 10/203,031

(22) PCT Filed: Jan. 18, 2001

(86) PCT No.: PCT/EP01/00522

§ 371 (c)(1),
(2), (4) Date: Nov. 4, 2002

(87) PCT Pub. No.: WO01/57232

PCT Pub. Date: Aug. 9, 2001

(65) Prior Publication Data

US 2003/0186396 A1  Oct. 2, 2003

(30) Foreign Application Priority Data

Feb. 4, 2000  (DE) ................. 100 04 926

(51) Int. Cl.
*C12P 41/00* (2006.01)

(52) U.S. Cl. .................................... 425/280

(58) Field of Classification Search ............... None
See application file for complete search history.

(56) References Cited

U.S. PATENT DOCUMENTS

| | | | |
|---|---|---|---|
| 5,492,830 A | 2/1996 | Kalwass et al. | |
| 5,770,438 A | 6/1998 | Nakahama et al. | |
| 5,811,292 A | 9/1998 | Patel et al. | |

FOREIGN PATENT DOCUMENTS

| | | |
|---|---|---|
| DE | 4414273 | 4/1991 |
| DE | 4217506 | 5/1992 |
| EP | 552041 | 7/1993 |
| EP | 709465 | 5/1996 |
| EP | 0 753 506 A | 1/1997 |
| EP | 0780369 | 6/1997 |
| JP | 05246918 | 11/1991 |
| JP | 07101921 | 10/1993 |
| JP | 08322590 | 12/1996 |
| JP | 09121564 | 5/1997 |
| WO | 9325703 | 6/1992 |
| WO | WO 98/40053 A | 9/1998 |

OTHER PUBLICATIONS

Gais et al., "Enzymztic resolutionof analgesics:gamma-hydroxytramadol, epsilon-hydroxytramadol and O-desmethyltramadol", Tetrahedron:Asymmetry 11 (2000) 917-928.*

Robert B. Raffa, et al., "Opioid and Nonopioid Components Independently Contribute to the Mechanism of Action of Tramadol, an 'Atypical' Opioid Analegesic" The Journal of Pharmacology and Experimental Therapeutics, vol. 260, No. 1, 1992, pp. 275-285.

Robert B. Raffa, et al., "Complementary and Synergistic Antinociceptive Interaction between the Enantiomers of Tramadol" The Journal of Pharmacology and Experimental Therapeutics, vol. 260, No. 1, 1992, pp. 331-340.

S.M. Roberts, et al., "The Use of Enzymes for the Preparation of Biologically Active Natural Products and Analogues in Optically Active Form" Current Organic Chemistry, vol. 1, 1997, pp. 1-20.

Gais et al., "Enzymatic resolution of analgesics: δ-hydroxytramadol, ε-hydroxytramadol and O-desmethyltramadol," Tetrahedron: Asymmetry, Mar. 2000, pp. 917-928, vol. 11, No. 4, Elsevier Science Publishers, Amsterdam.

Forro et al., "Enzymatic resolution of 2-dialkylaminomethylcyclopentanois and -cycloheptanols," Tetrahedron: Asymmetry, May 21, 2999, pp. 1985-1993, vol. 10, No. 10, Elsevier Science Publishers, Amsterdam.

Luna et al., "Enzymatic resolution of (±)-cis- and (±)-trans-1-aminoindan-2-ol and (±)-cis- and (±)-trans-2-aminoindan-1-ol," Tetrahedron: Asymmetry, May 21, 1999, pp. 1969-1977, Pergamon, Elsevier Science, NY, US.

Forro et al., "Lipase-catalysed resolution of 2-dialkylaminomethylcyclohexanols," Tetrahedron: Asymmetry, Feb. 13, 1999 pp. 513-520, vol. 9, No. 3, Elsevier Science Publishers, Amsterdam.

Frankus et al., "Uber die Isomerentrennung, Strukturaufklarung und pharmakologische Charakterisierung von 1-(m-Methoxyphenyl)-2-(dimethylaminomethyl)-cyclohexan-1-ol," Arzneimittel Forschung, Drug Research, 1978, pp. 114-121, vol. 28, No. 1A, Editio Cantor Aulendorf, Germany.

Poulsen et al., "The hypoalgesic effect of tramadol in relation to CYP2D6," Clinical Pharmacology & Therapeutics, Dec. 1, 1996, pp. 636-644, vol. 60, No. 6, Mosby-Year Book, St. Louis, MO, USA.

* cited by examiner

Primary Examiner—Sandra E. Saucer
(74) Attorney, Agent, or Firm—Crowell & Moring LLP

(57) ABSTRACT

The invention relates to a process for the enzymatic cleavage of racemates of aminomethyl-aryl-cyclohexanol derivatives.

31 Claims, No Drawings

METHOD FOR THE ENZYMATIC RESOLUTION OF THE RACEMATES OF AMINOMETHYL-ARYL-CYCLOHEXANOL DERIVATIVES

The invention relates to a process for the enzymatic cleavage of racemates of aminomethyl-aryl-cyclohexanol derivatives.

Treatment of chronic and non-chronic states of pain is of great importance in medicine. There is a worldwide need for pain treatments with a good action for target-orientated treatment of chronic and non-chronic states of pain appropriate for the patient, by which is to be understood successful and satisfactory pain treatment for the patient. This is documented in the large number of scientific works which have been published in the field of applied analgesics and basic research in nociception in recent years.

Tramadol hydrochloride-(1RS,2RS)-2-[(dimethylamino) methyl]-1-(3-methoxyphenyl)cyclohexanol hydrochloride—is a known therapeutic for treatment of severe pain. Aminomethyl-aryl-cyclohexanol derivatives such as tramadol ((1RS,2RS)-2-dimethylaminomethyl-1-(3-methoxyphenyl)-cyclohexanol hydrochloride) can accordingly have an analgesic action, as well as hydroxylated tramadol derivatives, such as are described e.g. in EP 753506 A1, or they can be used as intermediates for the preparation of substances having an analgesic action (such as e.g. 4- or 5-substituted tramadol analogues, which are described in EP 753 506 A1 or EP 780 369 A1). Precisely tramadol occupies a special position among analgesics having an action on the central nervous system in as much as this active compound brings about potent inhibition of pain without the side effects known of opioids (J. Pharmacol. Exptl. Ther. 267, 331 (1993)), both the enantiomers of tramadol and the enantiomers of tramadol metabolites participating in the analgesic action (J. Pharmacol. Exp. Ther. 260, 275 (1992)).

As can be seen from this, enantiomers can have significantly different actions, and in many respects it is very important also to be able to separate racemates into enantiomerically pure forms as intermediates or in respect of approvals under drug legislation.

Enzymatic transformations have since become the basic operations of preparative organic chemistry. Numerous industrial processes with enzymatic key steps which now go far beyond enzymatic cleavage of racemates of amino acids have also become established in the meantime. A more up-to-date overview of the use of enzymes in the preparation of biologically active compounds is given by Roberts and Williamson (S. M. Roberts, N. M. Williamson, *Current Organic Chemistry*, 1997, volume 1, 1–20).

Luana et al. (A. Luna, A. Maestro, C. Astorga, V. Gotor, *Tetrahedron: Asymmetry* 1999, 10, 1969–1977) describe the enzymatic cleavage of racemates via transesterification of cyclic α-aminoalcohols using lipases and vinyl acetate as the acyl donor. This publication is of importance since it is shown that substrates with an aminoalcohol functionality can be used.

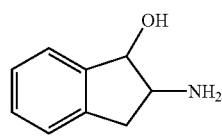

Forró and Fülöp (E. Forró, F. Fülöp, *Tetrahedron: Asymmetry* 1999, 10, 1985–1993, E. Forró, L. Kanerva, F. Fülöp, *Tetrahedron: Asymmetry* 1998, 9, 513–520) describe the enzymatic cleavage of racemates of reduced cyclic Mannich bases of the following type:

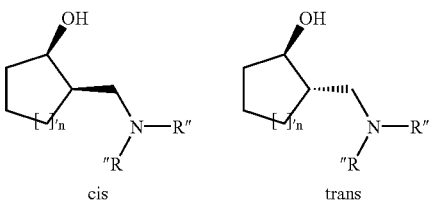

where n=1,2,3 and R'''=alkyl, alkylaryl, cycloalkyl

The authors make reference to tramadol in the introduction, and in the introductory text refer to the use of these compounds as units for substances potentially having an analgesic action.

In the development of enzymatic processes, in addition to the suitable enzyme system, discovery of suitable reaction parameters is decisive for the success of the process.

Preparation of enantiomerically pure aminomethyl-arylhexanol derivatives, in particular 4- or 5-hydroxylated tramadol derivatives, via fractional crystallization of diastereomeric salts, such as e.g. tartrates, dibenzoyltartrates or dobenzoyltartrates, has so far not been successful. Preparative chromatographic processes can be employed only in certain cases for providing enantiomerically pure compounds on a multigram scale. Suitable chromatographic conditions of preparative separation have also not yet been found.

The object of the present invention was therefore to discover suitable processes for enantiomerically pure separation of the enantiomers of aminomethyl-aryl-hexanol derivatives, in particular 4- or 5-hydroxylated tramadol derivatives—also on a larger scale.

The invention therefore provides processes for the enzymatic cleavage of racemates of aminomethyl-aryl-cyclohexanol derivatives of the general formula I

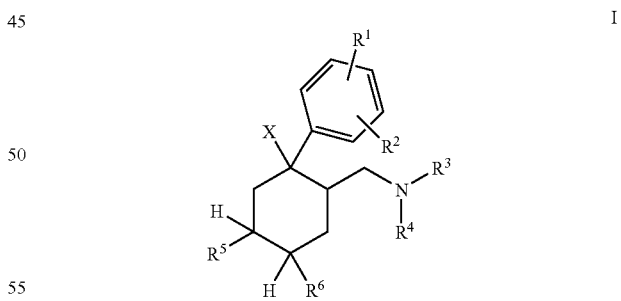

wherein X is chosen from
H, F, Cl, Br, I, $CF_3$, O—$S(O_2)$—$C_6H_4$-p$CH_3$, $OR^{14}$ or $OC(O)R^{14}$, wherein $R^{14}$ is chosen from
H; $C_1$–$C_{10}$-alkyl, $C_2$–$C_{10}$-alkenyl or $C_2$–$C_{10}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical in which a C atom in the ring is replaced by N, S or O; alkylaryl or alkylheteroaryl, saturated or unsaturated and mono- or polysubstituted or unsubstituted; aryl or heteroaryl, in each case mono- or polysubstituted or unsubstituted;

$R^3$, $R^4$ independently of one another are chosen from

H, $C_1$–$C_{10}$-alkyl, $C_2$–$C_{10}$-alkenyl or $C_2$–$C_{10}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical in which a C atom in the ring is replaced by N, S or O; alkylaryl or alkylheteroaryl, saturated or unsaturated and mono- or polysubstituted or unsubstituted; aryl or heteroaryl, in each case mono- or polysubstituted or unsubstituted;

or $R^3$ and $R^4$ together form a $C_3$–$C_7$-cycloalkyl, saturated or unsaturated and mono or polysubstituted or unsubstituted, or a corresponding heterocyclic radical in which a C atom in the ring is replaced by S, O or $NR^{15}$, where $R^{15}$ is chosen from H, $C_1$—$C_{10}$-alkyl, $C_2$–$C_{10}$-alkenyl or $C_2$–$C_{10}$-alkinyl, in each case branched or unbranched and mono- or polysubstituted or unsubstituted;

$R^1$ and $R^2$ independently of one another are either H or any desired substituent and in each case one of the substituents $R^5$ and $R^6$ corresponds to H and the other corresponds to OH, characterized in that, depending on the desired enantiomer of the aminomethyl-aryl-cyclohexanol derivatives of the general formula I either in reaction alternative I the racemate of compounds according to formula I is first esterified and then transformed enzymatically and the enantiomerically pure compounds formed are separated or in reaction alternative II the racemate of compounds according to formula I is transformed enzymatically in the presence of an ester and the enantiomerically pure compounds formed are separated.

These processes utilize in particular the fact that reaction alternatives I and II are to be regarded as complementary processes, since in the enzymatic transformation of the racemic mixture the particular opposite stereochemistry is induced.

In reaction alternative I, a racemic compound according to formula II

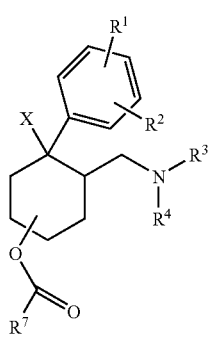

II in which the substituent $OC(O)R^7$ corresponds to the position of $R^5$ or $R^6$ in formula I and $R^7$ is chosen from $C_1$–$C_6$-alkyl, unsubstituted or mono- or polysubstituted; as the free base or in the form of its salt, is transformed enzymatically in a solvent with a lipase or esterase and the enantiomerically pure compounds formed, according to formulae III and Ia

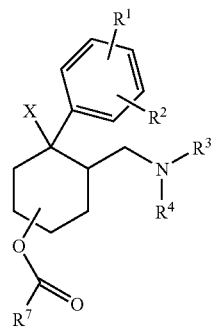

III

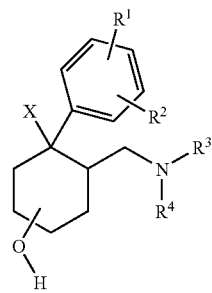

Ia where compounds according to formula Ia correspond to compounds according to formula I and the substituent OH corresponds to the position of $R^5$ or $R^6$ in formula I, are separated.

It is particularly preferable in reaction alternative I if $R^7$ in formulae II and III is chloroacetyl, butyl or pentyl.

An esterase, in particular a pig liver esterase, is preferably used as the enzyme in reaction alternative I.

The preferred solvent in reaction alternative I is an aqueous buffer system, which preferably has a pH of between 6.0 and 8.0—preferably a pH of between 7.0 and 7.5. It is also favourable here if the solvent is an aqueous buffer system with a physiological pH for the enzyme used. It is particularly favourable here if one or more organic solvent(s), preferably acetone or butanol, is/are added to the aqueous buffer system up to a percentage content by volume of between 1 and 50%, preferably 5 and 20%, in particular 20%.

It is furthermore preferable, in particular in the case of an aqueous buffer system, to employ the compound according to formula II as the hydrochloride salt in reaction alternative I.

It is of particular importance here that in the enzymatic hydrolysis of the butyric acid ester of 4-hydroxytramadol in particular, but also in other cases according to reaction alternative I—precisely with an aqueous buffer system—the use of the salt, in particular the hydrochloride, and not the base can lead to better results. The base is often not soluble in a sufficient amount in the aqueous buffer system. It is furthermore particularly remarkable that a significant improvement in the process, in particular also when the hydrochloride is employed, is to be observed if acetone and butanol are added. This particularly applies to the rate of reaction. In particular, an addition of acetone or butanol to the aqueous buffer in an amount of up to between 5 and 20%, preferably 20%, of the total volume is often optimum in respect of selectivity and rate of reaction.

The use of amino-hydrochlorides in enzymatic separations also has not hitherto been described in the prior art.

To prepare the ester of the compounds according to formula II in reaction alternative I, racemic compounds according to formula I

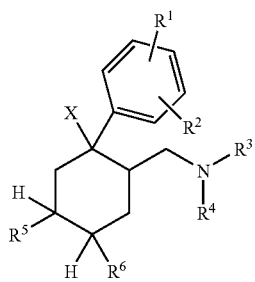

I are converted with bases, preferably potassium tert-butylate or sodium hydride, in a solvent, preferably tetrahydrofuran or dimethylformamide, into the alcoholates and subsequently, with the addition of corresponding acid halides, into the racemic esters according to formula II

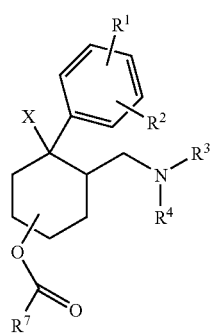

II in which the substituent OC(O)R$^7$ corresponds to the position of R$^5$ or R$^6$ in formula I. The esters according to formula II can preferably be prepared in this way.

In reaction alternative II, a racemic compound according to formula I

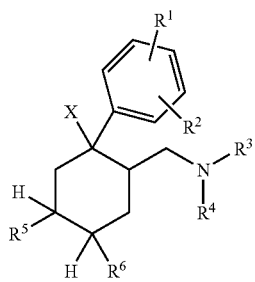

I employed as the free base or in the form of its salt in a solvent with an ester according to formula IV

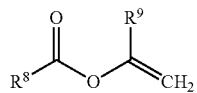

IV wherein, independently of one another, R$^8$ denotes $C_1$–$C_6$-alkyl, substituted or unsubstituted; and R$^9$ denotes H or $C_1$–$C_6$-alkyl, substituted or unsubstituted, is transformed enzymatically with a lipase or esterase and the enantiomerically pure compounds formed, according to formulae V and Ib

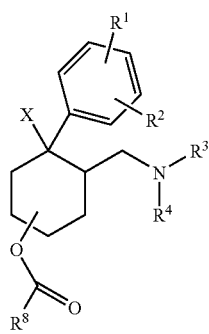

V

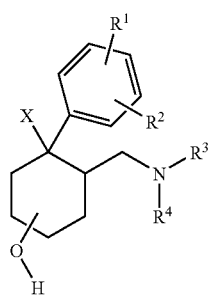

Ib wherein compounds according to formula Ib correspond to compounds according to formula I and the substituent OH corresponds to the position of R$^5$ or R$^6$ in formula I, are separated.

It is particularly preferable here if, in reaction alternative II, R$^8$ in the esters according to formulae IV and V denotes methyl or ethyl and/or R$^9$ according to formula IV denotes H or methyl.

In particular, the ester according to formula IV is preferably vinyl propionate, vinyl acetate or isopropenyl acetate.

A lipase, in particular a lipase from *Candida rugosa, Candida cylindracea* or *Pseudomonas cepacia*, is preferably used as the enzyme in reaction alternative II.

It has also proved particularly favourable to use an organic solvent, preferably toluene, as the solvent in reaction alternative II.

A decisive advantage of the process according to the invention by both reaction alternatives is the easily achievable separation of the enantiomerically pure compounds after conclusion of the enzymatic transformation. The ester/alcohol mixtures here are separated by pH-selective extraction after conclusion of the enzymatic transformation. A chromatographic separation can advantageously be omitted. By establishing a suitable pH, the ester and alcohol can be separated from one another by extraction, in particular by pH-selective extraction, on the basis of sufficiently different log P values. Scaling-up is therefore possible without problems and is particularly easy to carry out industrially.

The enzymatic processes found, by both reaction alternatives, are currently the only possibility of preparing aminomethyl-aryl-cyclohexanol derivatives, in particular hydroxylated tramadol derivatives, on a multigram scale with adequate purity of the enantiomers.

Overall, but in particular in the ester cleavage according to reaction alternative I, the conversion can be conducted to up to almost 50% without the selectivity being reduced drastically, as in many comparable enzymatic cleavages of racemates. Over-hydrolysis was not to be observed under the reaction conditions used.

It is furthermore particularly preferable that the substituents $R^1$ and $R^2$ in the formulae I, Ia, Ib, II, III and V independently of one another are chosen from $R^{10}$ or $YR^{10}$, where $Y=C_1-C_{10}$-alkyl, $C_2-C_{10}$-alkenyl or $C_2-C_{10}$-alkinyl, branched or unbranched and mono- or polysubstituted or unsubstituted, wherein $R^{10}$ is chosen from H, F, Cl, Br, I, CN, NO$_2$, $C_1-C_8$-alkyl, $C_2-C_8$-alkenyl or $C_2-C_8$-alkinyl, in each case branched or unbranched and mono- or polysubstituted or unsubstituted; $C_3-C_7$-cycloalkyl, saturated or unsaturated and mono- or polysubstituted or unsubstituted, or a corresponding heterocyclic radical in which a C atom in the ring is replaced by S, O or N; aryl or heteroaryl, in each case mono- or polysubstituted or unsubstituted;

$OR^{11}$, $OC(O)R^{11}$, $OC(O)OR^{11}$, $OC(S)R^{11}$, $C(O)R^{11}$, $C(O)OR^{11}$, $C(S)R^{11}$, $C(S)OR^{11}$, $SR^{11}$, $S(O)R^{11}$ or $S(O_2)R^{11}$, wherein $R^{11}$ is chosen from H, $C_1-C_{18}$-alkyl, $C_2-C_{18}$-alkenyl or $C_2-C_{18}$-alkinyl, in each case branched or unbranched and mono- or polysubstituted or unsubstituted; $C_3-C_7$-cycloalkyl, saturated or unsaturated and mono- or polysubstituted or unsubstituted, or a corresponding heterocyclic radical in which a C atom in the ring is replaced by S, O or N; alkylaryl or alkylheteroaryl, saturated or unsaturated and mono- or polysubstituted or unsubstituted; aryl or heteroaryl, in each case mono- or polysubstituted or unsubstituted; or $NR^{12}R^{13}$, $C(O)NR^{12}R^{13}$ or $S(O_2)NR^{12}R^{13}$, wherein $R^{12}$ and $R^{13}$ independently of one another are chosen from H, $C_1-C_{18}$-alkyl, $C_2-C_{18}$-alkenyl or $C_2-C_{18}$-alkinyl, in each case branched or unbranched and mono- or polysubstituted or unsubstituted; $C_3-C_7$-cycloalkyl, saturated or unsaturated and mono- or polysubstituted or unsubstituted, or a corresponding heterocyclic radical in which a C atom in the ring is replaced by S, O or N; alkylaxyl or alkylheteroaryl, saturated or unsaturated and mono- or polysubstituted or unsubstituted; aryl or heteroaryl, in each case mono- or polysubstituted or unsubstituted;

or $R^{12}$ and $R^{13}$ together form a $C_3-C_7$ cycloalkyl, saturated or unsaturated and mono- or polysubstituted or unsubstituted, or a corresponding heterocyclic radical in which a C atom in the ring is replaced by S, O or N;

or $R^1$ and 2 together form —CH═CH—CH═CH—, wherein the naphthyl system formed can be mono- or polysubstituted.

The following definitions apply to the complete description of the entire invention described here, and in particular also the sections and definitions of radicals presented above, unless expressly defined otherwise.

In connection with alkyl, alkenyl, alkinyl and cycloalkyl or the "corresponding heterocyclic radical", the term substituted here is understood in the context of this invention as replacement of a hydrogen radical by F, Cl, Br, I, NH$_2$, SH or OH, polysubstituted radicals being understood as radicals which are polysubstituted both on different and on the same atoms, for example trisubstituted on the same C atom, as in the case of CF$_3$, or at different points, such as in the case of —CH(OH)—CH═CH—CHCl$_2$.

Furthermore, —C(O)— denotes

which also applies to —C(S)— or —S(O)— or —S(O$_2$)—.

The term "$C_1-C_8$-alkyl" or "$C_1-C_{10}$-alkyl" in the context of this invention denotes hydrocarbons having 1 to 8 or 10 carbon atoms respectively. Examples which may be mentioned are methyl, ethyl, propyl, isopropyl, n-butane, sec-butyl, tert-butyl, n-pentane, neopentyl, n-hexane, n-heptane, n-octane, n-nonane or n-decane.

The term "$C_1-C_{18}$-alkyl" in the context of this invention denotes hydrocarbons having 1 to 18 carbon atoms. Examples which may be mentioned are methyl, ethyl, propyl, isopropyl, n-butane, sec-butyl, tert-butyl, n-pentane, neopentyl, n-hexane, n-heptane, n-octane, n-nonane, n-decane, n-undecane, n-dodecane, n-dodecane, n-tridecane, n-tetradecane, n-pentadecane, n-hexadecane, n-heptadecane or n-octadecane, unsubstituted or mono- or polysubstituted.

The term "$C_2-C_{10}$-alkenyl" or "$C_2-C_{10}$-alkinyl" or "$C_2-C_{18}$-alkenyl" or "$C_2-C_{18}$-alkinyl" in the context of this invention denotes hydrocarbons having 2 to 8 or 2 to 18 carbon atoms respectively. Examples which may be mentioned are propenyl, butenyl, pentenyl, hexenyl, heptenyl, octenyl, unsubstituted or mono- or polysubstituted, or propinyl, butinyl, pentinyl, hexinyl, heptinyl, octinyl, unsubstituted or mono- or polysubstituted.

The term $C_3-C_7$-cycloalkyl in the context of this invention denotes cyclic hydrocarbons having 3 to 7 carbon atoms. Examples which may be mentioned are cyclopropyl, cyclobutyl, cyclopentyl, cyclohexyl, cycloheptyl, cyclopentenyl, cyclohexenyl or cycloheptenyl, saturated or unsaturated and substituted or mono- or polysubstituted. A "corresponding heterocyclic radical" here in the context of the invention is understood as a $C_3-C_7$-cycloalkyl in which at least one C atom in the ring is replaced by S, O or N. Examples of these which may be mentioned are pyrrolidine, pyran, thiolane, piperidine or tetrahydrofuran.

The term "aryl" in the context of this invention denotes phenyls, naphthyls or anthracenyls. The aryl radicals can also be fused with further rings.

The term "heteroaryl" in the context of this invention denotes aromatic compounds which are optionally provided with a fused-on ring system and contain at least one heteroatom from the group consisting of nitrogen, oxygen and/or sulfur. Examples which may be mentioned in this group are thiophene, furan, pyrrole, pyridine, pyrimidine, quinoline, isoquinoline, phthalazine or quinazoline.

The term "alkylaryl" or "alkylheteroaryl" in the context of this invention denotes aryls or heteroaryls, where the terms aryl, heteroaryl and alkyl have the same meaning as above, which are substituted at least by $C_1$–$C_6$-alkylene and in which bonding is via the alkyl radical.

In respect of "aryl", "alkylaryl", "heteroaryl" or "alkylheteroaryl", in the context of this invention mono- or polysubstituted is understood as meaning substitution of the ring system by F, Cl, Br, X, $NH_2$, SH, OH, $CF_3$; =O or =S; mono- or polysubstituted or unsubstituted $C_1$–$C_6$-alkyl, $C_1$–$C_6$-alkoxy, $C_2$–$C_8$-alkenyl, $C_2$–$C_8$-alkinyl; phenyl or benzyl; on one or different atoms.

It is particularly advantageous if $R^1$ in the formulae I, Ia, Ib, II, III and V is $R^{10}$, wherein $R^{10}$ is chosen from H, F, Cl, Br, I, $CF_3$, $NO_2$, $NH_2$; $C_1$–$C_4$-alkyl or $C_2$–$C_4$-alkenyl, branched or unbranched and mono- or polysubstituted or unsubstituted; $OR^{11}$, $C(O)OR^{11}$ or $SR^{11}$, wherein $R^{11}$ is chosen from
H; $C_1$–$C_4$-alkyl, branched or unbranched and mono- or polysubstituted or unsubstituted; preferably H, $CF_3$ or $CH_3$,
or $S(O_2)NR^{12}R^{13}$, wherein $R^{12}$ and $R^{13}$ independently of one another are chosen from
H; $C_1$–$C_4$-alkyl, branched or unbranched and mono- or polysubstituted or unsubstituted;

wherein $R^1$ is particularly preferably chosen from
H, F, Cl, OH, $CH_3$, $C_2H_5$, $C_2H_3$, $CF_3$, $SCH_3$, $OCF_3$, $OCH_3$, $OC_2H_5$, $C(O)OCH_3$, $C(O)OC_2H_5$, preferably m-$OCH_3$.

In particular, the substituent $R^2$ in the formulae I, Ia, Ib, II, III and V can be $R^{10}$, wherein $R^{10}$ is chosen from
H, F, Cl, Br, I, $SCH_3$; $C_1$–$C_4$-alkyl, $C_2$–$C_4$-alkenyl, branched or unbranched and mono- or polysubstituted or unsubstituted, preferably $CF_3$; $OR^{11}$, where $R^{11}$ is chosen from $C_1$–$C_4$-alkyl, branched or unbranched and mono- or polysubstituted or unsubstituted, preferably $CH_3$;

wherein $R^2$ particularly preferably=H.

It is furthermore particularly preferable if X in the formulae I, Ia, Ib, II, III and V is chosen from
H, F, Cl, OH, $CF_3$, O—$S(O_2)$—$C_6H_4$-p$CH_3$ or OC(O)$R^{12}$ where $R^{12}$=H; $C_1$–$C_4$-alkyl or $C_2$–$C_4$-alkenyl, branched or unbranched and mono- or polysubstituted or unsubstituted,
preferably H, F, Cl, OH, O—$S(O_2)$—$C_6H_4$-p$CH_3$, OC(O)$R^{12}$, where $R^{12}$=$C_1$–$C_4$-alkyl, preferably $CH_3$;

wherein X is particularly preferably OH, F or Cl, preferably OH.

It is furthermore a preferred subject matter of the invention if $R^3$ and $R^4$ in the formula I, II, III and V independently of one another are chosen from
$C_1$–$C_4$-alkyl, branched or unbranched and mono- or polysubstituted or unsubstituted, preferably $CH_3$,
or
$R^3$ and $R^4$ together form a $C_3$–$C_7$-cycloalkyl, saturated or unsaturated and mono- or polysubstituted or unsubstituted, Wherein $R^3$ and $R^4$ particularly preferably each denote $CH_3$.

The invention also furthermore provides intermediate products according to formula II. The definition of the radicals $R^1$–$R^4$ and X and $R^7$ mentioned has already been described above, as has also a preferred preparation process for products according to formula II in the context of reaction alternative I. The compounds according to formula II are very suitable analgesics and can also be employed for further indications. They are therefore suitable, in the form of their diastereomers or enantiomers and their free base or a salt formed with a physiologically tolerated acid, in particular the hydrochloride salt, for the preparation of a medicament for treatment of pain, in particular migraine, acute pain and neuropathic or chronic pain, of inflammatory and allergic reactions, depressions, drug and/or alcohol abuse, gastritis, cardiovascular diseases, respiratory tract diseases, coughing, mental illness and/or epilepsy, and in particular of urinary incontinence, itching and/or diarrhoea.

The invention is explained below in more detail by examples, without limiting it thereto.

EXAMPLES

The following examples show processes according to the invention.

The following information generally applies in these:

The chemicals and solvents employed were obtained commercially from the conventional suppliers (Acros, Avocado, Aldrich, Fluka, Lancaster, Maybridge, Merck, Sigma, TCI etc.) or synthesized.

Example 1

Preparation of the Carboxylic Acid Eaters of Hydroxytramadols (1SR,3RS,4RS)-Butyric acid 3-dimethylaminomethyl-4-hydroxy-4-(3-methoxy-phenyl)-cyclohexyl ester hydrochloride (rac-1)

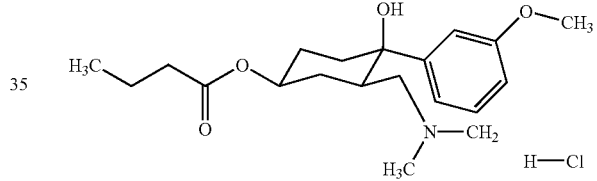

250 g (0.89 mol) (1RS,2RS,4SR)-2-dimethylaminomethyl-1-(3-methoxy-phenyl)-cyclohexane-1,4-diol rac-2 were suspended in 2,500 ml dried tetrahydrofuran, and 226 g potassium tert-butylate (2.01 mol) were added in portions, while cooling with an ice-bath such that the internal temperature did not exceed 30° C. When the addition had ended the mixture was subsequently stirred at room temperature for a further hour. 127 ml (130.3 g, 1.22 mol) butyric acid chloride were then added, while cooling with an ice-bath, the internal temperature being between 5 and 10° C. When the addition was complete, the mixture was subsequently stirred at room temperature for a further 15 hours. For hydrolysis, 1,187 ml of a 1 molar aqueous sodium bicarbonate solution were added dropwise, with renewed cooling with an ice-bath. After separation of the phases, the aqueous phase was extracted twice more with 500 ml ethyl acetate. The combined organic phases were dried over sodium sulfate. After removal of the solvent by distillation, the residue (277.4 g) was converted into the hydrochloride. For this, the 277.4 g of crude product were dissolved in a solvent mixture comprising 270 ml ethanol and 1,350 ml acetone. After addition of one molar equivalent of trimethylchlorosilane and one molar equivalent of water, the hydrochloride crystallized out. After the mixture had been left to stand at 15° C. for 15 hours, the precipitate was filtered off with suction and, after drying, 273.2 g hydrochloride could be obtained in a yield of 89%.

Example 2

Preparation of Carboxylic Acid Esters of Hydroxy-tramadols (1SR,3RS,4RS)-Butyric acid 4-dimethylaminomethyl-3-hydroxy-3-(3-methoxy-phenyl)-cyclohexyl ester hydrochloride (rac-3)

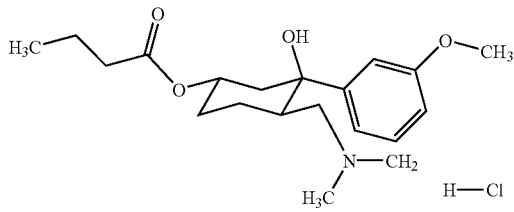

Analogously to the preparation of (1SR,3RS,4RS)-butyric acid 3-dimethylaminomethyl-4-hydroxy-4-(3-methoxy-phenyl)-cyclohexyl ester hydrochloride rac-1, the ester rac-3 could be obtained in a yield of 85% from (1RS,3SR,6RS)-6-dimethylatinomethyl-1-(3-methoxy-phenyl)-cyclohexane-1,3-diol rac-4.

Example 3

Enzymatic Ester Hydrolysis

Pig liver esterase-catalysed hydrolysis of (1SR,3RS,4RS)-butyric acid 3-dimethylaminomethyl-4-hydroxy-4-(3-methoxy-phenyl)-cyclohexyl ester hydrochloride (rac-1)

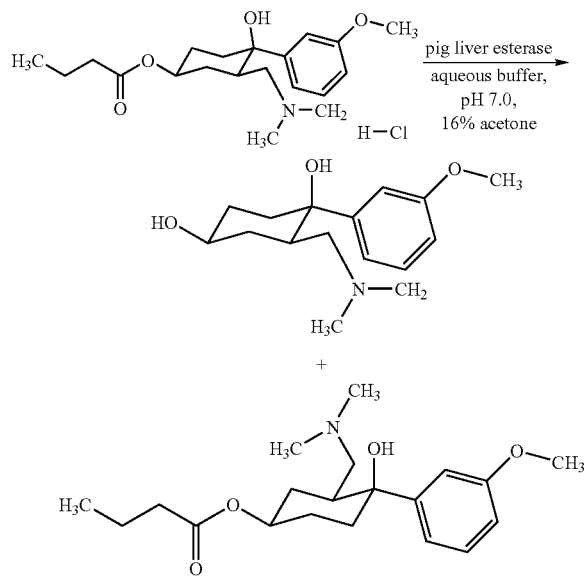

(−)-(1R,3S,4S)-Butyric acid 3-dimethylaminomethyl-4-hydroxy-4-(3-methoxy-phenyl)-cyclohexyl eater ((−)-1)

and (+)-(1R,2R,4S)-2-Dimethylaminomethyl-1-(3-methoxy-phenyl)-cyclohexane-1,4-diol ((+)-2)

72 g (0.19 mol) (1SR,3RS,4RS)-butyric acid 3-dimethylaminomethyl-4-hydroxy-4-(3-methoxy-phenyl)-cyclohexyl ester hydrochloride rac-1 were dissolved in 620 ml aqueous phosphate buffer solution pH 7 (Merck, art. no. 1.09439.100), and 140 ml acetone were added. After the mixture had been stirred for 10 minutes, a clear solution was formed. 0.62 g pig liver esterase (Chirazyme E1 from Roche Diagnostics, lyophilisate, 40 units/mg) and 150 ml of a 1 molar aqueous sodium bicarbonate solution were then added in one portion so that a pH of 7.5 was established. The reaction mixture was stirred at room temperature for 21 hours. To end the reaction, the buffer system was extracted twice with 450 ml diisopropyl ether each time and twice with a solvent mixture of diisopropyl ether and diethyl ether in a ratio of 1:1 each time, only the ester passing into the organic phase under these conditions and the hydrolysed alcohol remaining in the aqueous phase because of the different logP value (see table 1).

To isolate the ester (−)-1, the combined organic phases were washed once with 400 ml of a 1 molar aqueous sodium carbonate solution and dried over sodium sulfate. After removal of the solvent by distillation, 30.4 g of crude product (93% of theory) comprising (−)-(1R,3S,4S)-butyric acid 3-dimethylaminomethyl-4-hydroxy-4-(3-methoxy-phenyl)-cyclohexyl ester (−)-1 were obtained. The crude base ($[\alpha]_D^{22}=-12.0°$ (c=1.02, methanol)) was taken up in 300 ml of a solvent mixture comprising ethanol and 2-butanone in a ratio of 1:9, and 11.0 ml trimethylchlorosilane and 1.57 ml water were added. 3.6 g (10% of theory) of the hydrochloride crystallized out with an ee value of 4.8%. After separating off, the mother liquor was concentrated. After liberation of the base with sodium carbonate and extraction with ethyl acetate, drying over sodium sulfate and removal of the solvent by distillation, 23.9 g (73% of theory) (−)-(1R,3S,4S)-butyric acid 3-dimethylaminomethyl-4-hydroxy-4-(3-methoxy-phenyl)-cyclohexyl ester (−)-1 could be obtained with an ee value of 100% (determined by chiral HPLC). (−)-(1S,2S,4R)-2-Dimethylaminomethyl-1-(3-methoxy-phenyl)-cyclohexane-1,4-diol (−)-2 could be obtained from this in a quantitative yield by alkaline ester hydrolysis with potassium hydroxide in ethanol.

For isolation of (+)-(1R,2R,4S)-2-dimethylaminomethyl-1-(3-methoxy-phenyl)-cyclohexane-1,4-diol (+)-2, the aqueous phase of the ester hydrolysis was brought to a pH of 5.0 with 2 molar hydrochloric acid. The solution adjusted in this way was freed from the solvent at a bath temperature of 60° C. under a pressure of 650 mbar to 150 mbar. The residue was then brought to a pH of 10.0 with 2 molar aqueous sodium carbonate solution and the mixture was extracted three times with 100 ml ethyl acetate each time. The combined organic phases were dried over sodium sulfate. After removal of the solvent by distillation, 26.0 g (100% of theory) crude product could be obtained. The crude base was taken up in 270 ml of a solvent mixture comprising ethanol and 2-butanone in a ratio of 1:9, and 12.2 ml trimethylchlorosilane and 1.73 ml water were added, the hydrochloride of (+)-(1R,2R,4S)-2-dimethylaminomethyl-1-(3-methoxy-phenyl)-cyclohexane-1,4-diol (+)-2 crystallizing out in a yield of 78% (23.1 g) with an ee value of 96.3% (according to chiral HPLC) ($[\alpha]_D^{22}=+36.5°$ (c=1.06 methanol)).

The following table 1 shows the pKa values and logP values of the compounds 1 and 2.

TABLE 1 pKa values and logP values of the compounds 1 and 2.

|  | Compound 1 (ester) | Compound 2 (alcohol) |
| --- | --- | --- |
| pKa value | 8.796 | 9.055 |
| logP value: water/octanol | 2.898 | 1.101 |

TABLE 1-continued pKa values and logP values of the compounds 1 and 2.

|  | Compound 1 (ester) | Compound 2 (alcohol) |
| --- | --- | --- |
| logP value: water/cyclohexane | 2.360 | −0.632 |
| logD value at pH 7.4 water/octanol | 1.484 | −0.564 |
| logD value at pH 7.4 water/cyclohexane | 0.946 | −2.297 |
| ΔlogP value at pH 7.4 | 0.538 | 1.733 |
| ΔlogD value at pH 7.4 | 0.538 | 1.733 |

The following table 2 shows the dependency of the ee value of the ester and alcohol as a function of the reaction time by way of example.

TABLE 2

Dependency of the ee value of the ester and alcohol as a function of the reaction time (the content and ee value of compounds 1 and 2 were determined by means of chiral HPLC):

| Time in hours | Ester content in %[1] | (+) − Ester content[2] (in %) | (−) − Ester content[2] (in %) | % ee value of the (−) − ester[3] |
| --- | --- | --- | --- | --- |
| 3 | 91.2 | 40.8 | 50.4 | 10.5 |
| 19 | 68.6 | 17.7 | 50.9 | 48.4 |
| 24 | 64.4 | 14.0 | 50.4 | 56.6 |
| 28 | 62.2 | 11.4 | 50.9 | 63.4 |

| | Alcohol content in %[1] | (−) − Alcohol content[2] (in %) | (+) − Alcohol content[2] (in %) | % ee value of the (+) − alcohol[3] |
| --- | --- | --- | --- | --- |
| 3 | 8.8 | 0.4 | 8.4 | 91.6 |
| 19 | 31.4 | 0.5 | 30.9 | 96.6 |
| 24 | 35.6 | 0.7 | 35.0 | 96.2 |
| 28 | 37.8 | 0.7 | 37.1 | 96.5 |

[1] percentage content of ester or alcohol relates to the total content of ester and alcohol determined in the reaction mixture;
[2] the percentage content of enantiomeric esters or alcohols relates to the content of ester and alcohol in the total mixture ((+) − enantiomer (ester) + (−) − enantiomer (ester) + (+) − enantiomer (alcohol) + (−) − enantiomer (alcohol) = 100%;
[3] the percentage ee value was determined according to the following equation: % excess enantiomer − % deficit enantiomer/% excess enantiomer + % deficit enantiomer.

The dependency of the % ee value of the alcohol (+)-2 on the amount of acetone added is shown in table 3:

TABLE 3

Dependency of the % ee value of the alcohol (+) − 2 on the amount of acetone added (1.5 mmol ester rac-1 as the hydrochloride were dissolved in 5 ml phosphate buffer pH 7.0 (Merck), and 1.2 ml of a 1 molar aqueous sodium bicarbonate solution were added; the amount of enzyme added was 5.0 mg Chirazyme El from Roche Diagnostics; the mixture was stirred for in each case 19 hours at room temperature; working up was carried out as described in example 1)

| Addition of acetone (ml, %) | Total ester content[1] (in %) | % ee value of the (−) − ester[2] | Total alcohol content[1] (in %) | % ee value of the (+) − alcohol[2] |
| --- | --- | --- | --- | --- |
| 0 ml, 0% | 46.1 | 90.7 | 53.9 | 72.5 |
| 0.6 ml, 9% | 50.8 | 97.6 | 49.2 | 89.8 |
| 1.0 ml, 13.5% | 56.8 | 85.7 | 43.3 | 96.9 |
| 1.2 ml, 16% | 55.6 | 94.2 | 44.4 | 95.5 |

[1] the percentage content of the enantiomeric esters or alcohols relates to the content of ester and alcohol in the total mixture ((+) − enantiomer (ester) + (−) − enantiomer (ester) to (+) − enantiomer (alcohol) + (−) − enantiomer (alcohol);
[2] the percentage ee value was determined in accordance with the following equation: % excess enantiomer − % deficit enantiomer/% excess enantiomer + % deficit enantiomer.

Example 4

Enzymatic Ester Hydrolysis

Lipase-catalysed hydrolysis of (1SR,3RS,4RS)-butyric acid 3-dimethylaminomethyl-4-hydroxy-4-(3-methoxy-phenyl)-cyclohexyl ester (rac-1)

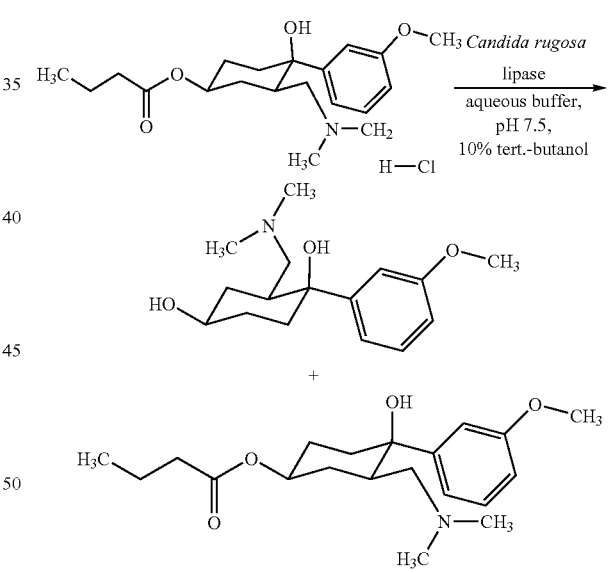

(+)-(1S,3R,4R)-Butyric acid 3-dimethylaminomethyl-4-hydroxy-4-(3-methoxy-phenyl)-cyclohexyl ester ((+)-1)

and (−)-(1S,2S,4R)-2-Dimethylaminomethyl-1-(3-methoxy-phenyl)-cyclohexane-1,4-diol ((−)-2)

Analogously to that described in example 3, enzymatic hydrolysis of rac-1 using the lipase *Candida rugosa* (Fluka) in an aqueous buffer system at a pH of 7.5 using 10% tert-butanol leads to an opposite asymmetric induction after a reaction time of 24 hours at room temperature. After a conversion of 28%, the alcohol (−)-2 could be isolated with an ee value of 89% and the ester (+)-1 with an ee value of 37% (E=24).

Example 5

Enzymatic Ester Hydrolysis

Pig liver esterase-catalysed hydrolysis of (1SR,3RS,4RS)-butyric acid 4-dimethylaminomethyl-3-hydroxy-3-(3-methoxy-phenyl)-cyclohexyl ester hydrochloride (rac-3)

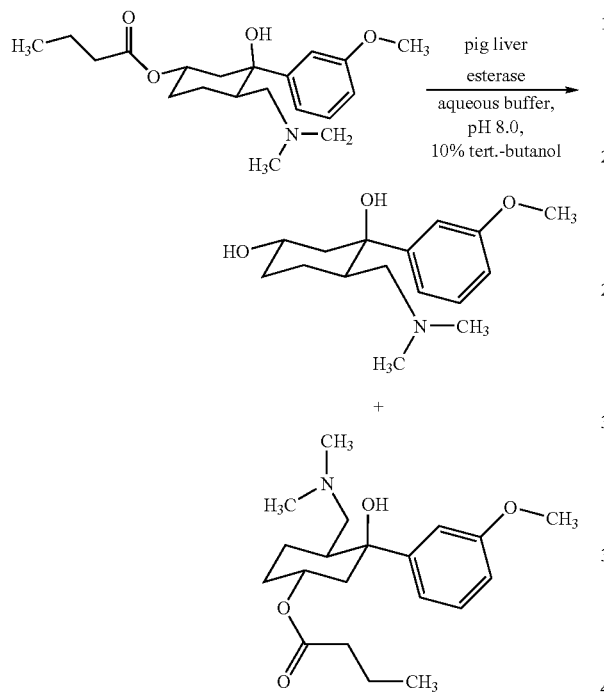

(+)-(1R,3S,6R)-6-Dimethylaminomethyl-1-(3-methoxy-phenyl)-cyclohexane-1,3-diol ((+)-4)

and (−)-(1R,3S,4S)-Butyric acid 4-dimethylaminomethyl-3-hydroxy-3-(3-methoxy-phenyl)-cyclohexyl ester ((−)-3)

Analogously to that described in example 3, enzymatic hydrolysis of rac-3 using pig liver esterase in an aqueous buffer system at a pH of 8.0 using 10% tert-butanol leads to a conversion of 40% after a reaction time of 6 hours at room temperature. It was possible in this manner to obtain the ester (−)-3 in a yield of 79% with an ee value of 86% ($[\alpha]_D^{22}$=−6.0° (c=0.81, methanol)) and the alcohol (+)-4 in a yield of 77% with an ee value of 94% ($[\alpha]_D^{22}$=+21.7° (c=0.80, methanol)) (E=46).

Example 6

Enzymatic Ester Hydrolysis

Lipase-catalysed hydrolysis of (1SR,3RS,4RS)-butyric acid 4-dimethylaminomethyl-3-hydroxy-3-(3-methoxy-phenyl)-cyclohexyl ester hydrochloride (rac-3)

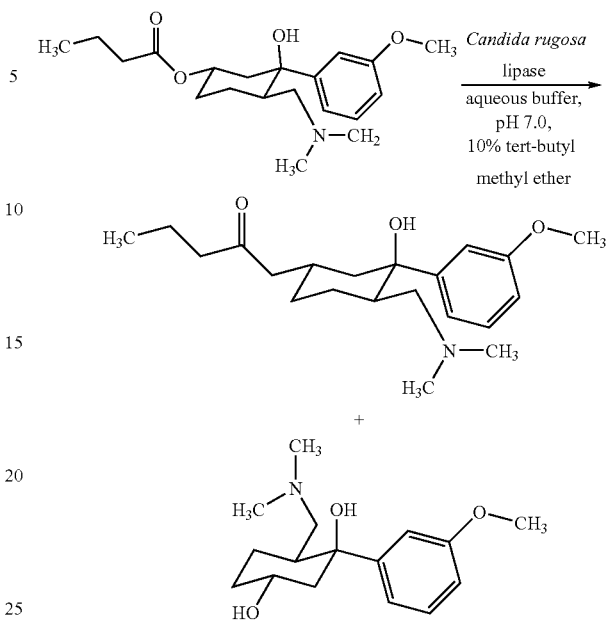

(−)-(1S,3R,6S)-6-Dimethylaminomethyl-1-(3-methoxy-phenyl)-cyclohexane-1,3-diol ((−)-4)

and (+)-(1S,3R,4R)-Butyric acid 4-dimethylaminomethyl-3-hydroxy-3-(3-methoxy-phenyl)-cyclohexyl ester ((+)-3)

Analogously to that described in example 3, enzymatic hydrolysis of rac-3 using the lipase Candida rugosa in an aqueous buffer system at a pH of 7.0 using 10% tert-butyl methyl ether leads to a conversion of 45% after a reaction time of 6 hours at room temperature. It was possible in this manner to obtain the eater (+)-3 in a yield of 80% with an ee value of >99% ($[\alpha]_D^{22}$=+7.5° (c=0.74, methanol)) and the alcohol (−)-4 in a yield of 79% with an ee value of >99% ($[\alpha]_D^{22}$=−29.5° (c=1.01, methanol)) (E>200).

Example 7

Enzymatic Transacylation in Organic Solvents

Lipase-catalysed transacylation of (1RS,3SR,6RS)-6-dimethylaminomethyl-1-(3-methoxy-phenyl)-cyclohexane-1,3-diol rac-4 with various acylating reagents to give the esters 5 and 6

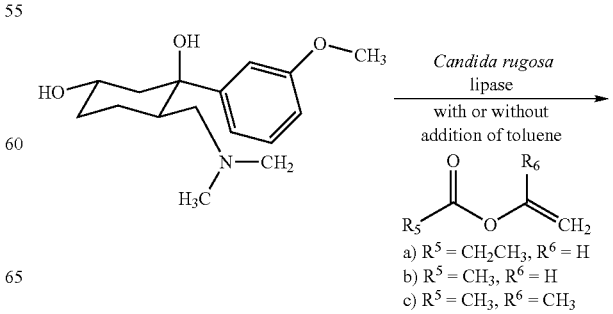

a) $R^5$ = CH$_2$CH$_3$, $R^6$ = H
b) $R^5$ = CH$_3$, $R^6$ = H
c) $R^5$ = CH$_3$, $R^6$ = CH$_3$

-continued

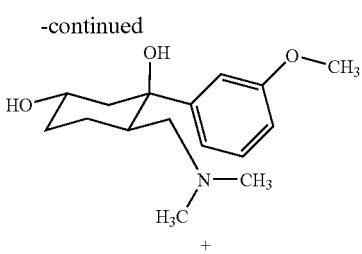

+

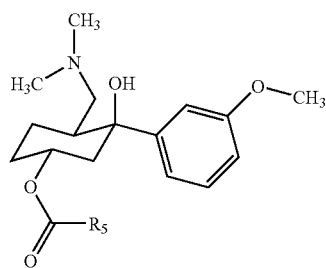

(1R,3S,6R)-6-Dimethylaminomethyl-1-(3-methoxy-phenyl)-cyclohexane-1,3-diol (+)-4 and $R^5=CH_3$: (−)-(1R,3S,4S)-Acetic acid 4-dimethylaminomethyl-3-hydroxy-3-(3-methoxy-phenyl)-cyclohexyl ester (−)-5 or $R^5=CH_2CH_3$; (−)-(1R,3S,4S)-Propionic acid 4-dimethylaminomethyl-3-hydroxy-3-(3-methoxy-phenyl)-cyclohexyl ester (−)-6

For the transacylation, 70 mg (0.25 mmol) (1RS,3SR,6RS)-6-dimethylaminomethyl-1-(3-methoxy-phenyl)-cyclohexane-1,3-diol rac-4 were taken up in a solvent mixture comprising toluene and the transacylating reagent or using the transacylating agent itself as the solvent, and the mixture was first stirred at room temperature for two hours. After addition of the lipase *Candida rugosa* (5 mg, 185 units), the mixture was stirred at room temperature for 5 to 9 days. To separate off the enzyme, the mixture was filtered over silica gel. The alcohol and ester were separated from one another as described in example 1 and isolated. The results are summarized in table 4.

Instead of the lipase *Candida rugosa*, the lipases *Candida cylindracea* or *Pseudomonas cepacia* were also employed in an analogous manner.

TABLE 4

Results of the enzymatic transacylation of (1RS,3SR,SRS)-6-dimethylaminomethyl-1-(3-methoxy-phenyl)-cyclohexane-1,3-diol rac-4

| Example no. | Transacylating reagent, solvent | Reaction time (days) | Conversion (%) | Ester | % ee value of the ester | Alcohol | % ee value of the alcohol | E value |
|---|---|---|---|---|---|---|---|---|
| 5a | 1.25 mmol propionic acid vinyl ester in 5 ml toluene | 9 | 48 | (−)-6 | 87 | (+)-4 | 68 | 30 |
| 5b | 53.75 mmol acetic acid vinyl ester without addition of toluene | 7 | 56 | (−)-5 | 91 | (+)-4 | 97 | 89 |
| 5c | 1.5 mmol acetic acid isopropenyl ester in 5 ml toluene | 5 | 34 | (−)-5 | 99 | (+)-4 | 60 | >200 |

Nomenclature Overview

| Formula | Nomenclature |
|---|---|
| | (1RS,2RS,4SR)-2-Dimethylaminomethyl-1-(3-methoxy-phenyl)-cyclohexane-1,4-diol |
| | (1RS,3RS,6RS)-6-Dimethylaminomethyl-1-(3-methoxy-phenyl)-cyclohexane-1,3-diol |
| | (1RS,3SR,6RS)-6-Dimethylaminomethyl-1-(3-methoxy-phenyl)-cyclohexane-1,3-diol |
| | (1SR,3RS,4RS)-Butyric acid 3-dimethylaminomethyl-4-hydroxy-4-(3-methoxy-phenyl)-cyclohexyl ester |
| | (1SR,3RS,4RS)-Butyric acid 4-dimethylaminomethyl-3-hydroxy-3-(3-methoxy-phenyl)-cyclohexyl ester |
| | (−)-(1R,3S,4S)-Acetic acid 4-dimethylaminomethyl-3-hydroxy-3-(3-methoxy-phenyl)-cyclohexyl ester |
| | (−)-(1R,3S,4S)-Propionic acid 4-dimethylaminomethyl-3-hydroxy-3-(3-methoxy-phenyl)-cyclohexyl ester |

The invention claimed is:

1. A process for the separating enantiomers of aminomethyl-aryl-cyclohexanol compounds corresponding to formula I

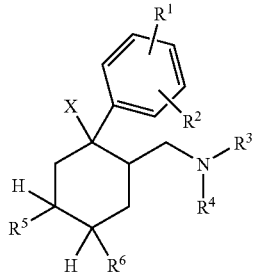

wherein X is chosen from
  H, F, Cl, Br, I, $CF_3$, $O-S(O_2)-C_6H_4$-$pCH_3$, $OR^{14}$ or $OC(O)R^{14}$, wherein $R^{14}$ is chosen from
    H; $C_1-C_{10}$-alkyl, $C_2-C_{10}$-alkenyl or $C_2-C_{10}$-alkinyl, in each case branched or unbranched and mono- or polysubstituted or unsubstituted; $C_3-C_7$-cycloalkyl, saturated or unsaturated and mono- or polysubstituted or unsubstituted, or a corresponding heterocyclic radical in which a C atom in the ring is replaced by N, S or O; alkylaryl or alkylheteroaryl, saturated or unsaturated and mono- or polysubstituted or unsubstituted; aryl or heteroaryl, in each case mono- or polysubstituted or unsubstituted;
$R^3$, $R^4$ independently of one another are chosen from
  H, $C_1-C_{10}$-alkyl, $C_2-C_{10}$-alkenyl or $C_2-C_{10}$-alkinyl, in each case branched or unbranched and mono- or polysubstituted or unsubstituted; $C_3-C_7$-cycloalkyl, saturated or unsaturated and mono- or polysubstituted or unsubstituted, or a corresponding heterocyclic radical in which a C atom in the ring is replaced by N, S or O; alkylaryl or alkylheteroaryl, saturated or unsaturated and mono- or polysubstituted or unsubstituted; aryl or heteroaryl, in each case mono- or polysubstituted or unsubstituted;
or
$R^3$ and $R^4$ together form a $C_3-C_7$-cycloalkyl, saturated or unsaturated and mono- or polysubstituted or unsubstituted, or a corresponding heterocyclic radical in which a C atom in the ring is replaced by S, O or $NR^{15}$, where $R^{15}$ is chosen from
  H, $C_1-C_{10}$-alkyl, $C_2-C_{10}$-alkenyl or $C_2-C_{10}$-alkinyl, in each case branched or unbranched and mono- or polysubstituted or unsubstituted;
$R^1$ and $R^2$ independently of one another are either H or any desired substituent
and
in each case one of the substituents $R^5$ and $R^6$ corresponds to H and the other corresponds to OH, characterized in that, depending on the desired enantiomer of the aminomethyl-aryl-cyclohexanol compounds corresponding to formula I
comprising, according to reaction I, esterifying compounds corresponding to formula I and enzymatically transforming the compounds and separating enantiomerically pure compounds
or comprising, according to reaction II, enzymatically transforming
compounds corresponding to formula I in the presence of an ester and separating enantiomerically pure compounds.

2. A process according to claim 1, comprising in reaction I, enzymatically transforming a compound corresponding to formula II

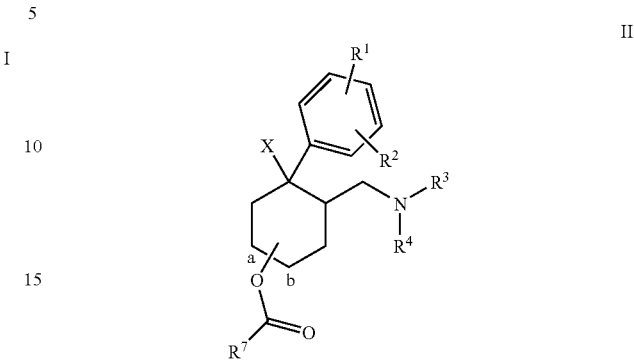

in which the substituent $OC(O)R^7$ corresponds to the position of $R^5$ or $R^6$ in formula I and $R^7$ is chosen from $C_1-C_6$-alkyl, unsubstituted or mono- or polysubstituted; as the free base or in the form of its salt, in a solvent with a lipase or esterase and separating enantiomerically pure compounds corresponding to formulae III and Ia

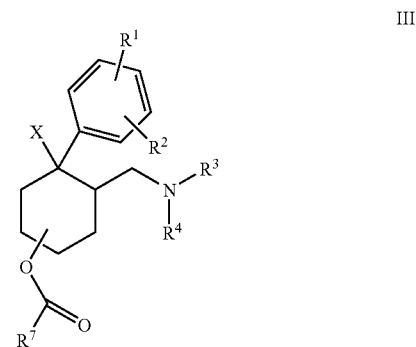

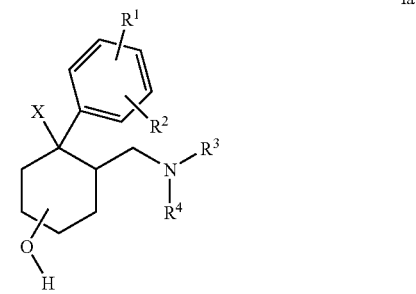

where compounds according to formula Ia correspond to compounds according to formula I and the substituent OH corresponds to the position of $R^5$ or $R^6$ in formula I.

3. The process according to claim 2, characterized in that $R^7$ is chloroacetyl, butyl or pentyl.

4. The process according to claim 2, characterized in that the enzyme used is an esterase.

5. The process according to claim 2, characterized in that an aqueous buffer system is used as the solvent.

6. The process according to claim 2, characterized in that an aqueous buffer system, preferably with a physiological pH for the enzyme used, is used as the solvent.

7. The process according to claim 5, characterized in that at least one organic solvent is added to the aqueous buffer system up to a percentage content by volume of between 1 and 50%.

8. The process according to claim 2, characterized in that the compound according to formula II is employed as the hydrochloride salt.

9. The process according to claim 2, characterized in that the compounds according to formula II employed are prepared by a process in which racemic compounds according to formula I

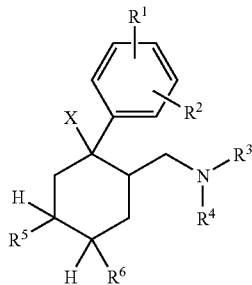

are converted with bases in a solvent into the alcoholates and subsequently, with the addition of corresponding acid halides, into the racemic esters according to formula II

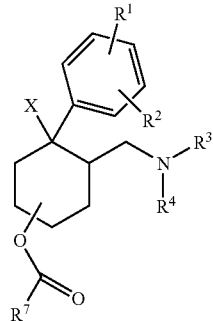

in which the substituent OC(O)R$^7$ corresponds to the position of R$^5$ or R$^6$ in formula I.

10. The process according to claim 1, comprising, in reaction alternative II, enzymatically transforming a racemic compound corresponding to formula I

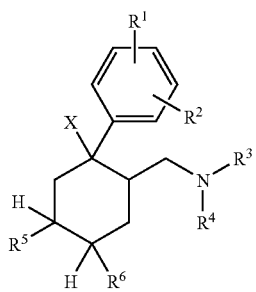

employed as the free base or in the form of its salt in a solvent with an ester according to formula IV

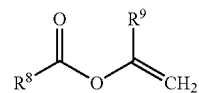

wherein, independently of one another, R$^8$ denotes C$_1$–C$_6$alkyl, substituted or unsubstituted; and R$^9$ denotes H or C$_1$–C$_6$-alkyl, substituted or unsubstituted, with a lipase or esterase and separating the enantiomerically pure compounds formed, corresponding to formulae V and Ib

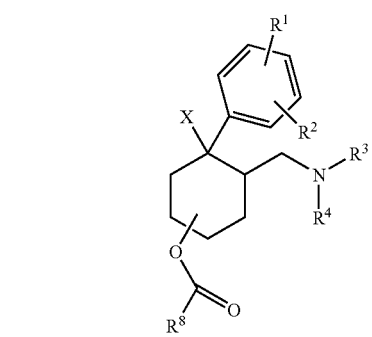

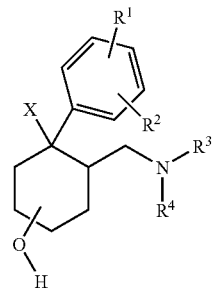

wherein compounds according to formula Ib correspond to compounds according to formula I and the substituent OH corresponds to the position of R$^5$ or R$^6$ in formula I.

11. The process according to claim 10, characterized in that in the esters according to formulae IV and V, R$^8$ denotes methyl or ethyl or R$^9$ according to formula IV denotes H or methyl.

12. The process according to claim 10, characterized in that the ester according to formula IV is vinyl propionate, vinyl acetate or isopropenyl acetate.

13. The process according to claim 10, characterized in that the enzyme used is a lipase.

14. The process according to claim 10, characterized in that an organic solvent is used as the solvent.

15. The process according to claim 1, characterized in that ester/alcohol mixtures are separated by pH-selective extraction after conclusion of the enzymatic transformation.

16. The process according to claim 1, characterized in that R$^1$ and R$^2$ in the formulae I, Ia, Ib, II, III and V independently of one another are chosen from R$^{10}$ or YR$^{10}$, where Y=C$_1$–C$_{10}$-alkyl, C$_2$–C$_{10}$-alkenyl or C$_2$–C$_{10}$-alkinyl, branched or unbranched and mono- or polysubstituted or unsubstituted, wherein $R^{10}$ is chosen from H, F, Cl, Br, I, CN, $NO_2$, $C_1$–$C_8$-alkyl, $C_2$–$C_8$-alkenyl or $C_2$–$C_8$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical in which a C atom in the ring is replaced by S, O or N; aryl or heteroaryl, in each case mono- or polysubstituted or unsubstituted;

$OR^{11}$, $OC(O)R^{11}$, $OC(O)OR^{11}$, $OC(S)R^{11}$, $C(O)R^{11}$, $C(O)OR^{11}$, $C(S)R^{11}$, $C(S)OR^{11}$, $SR^{11}$, $S(O)R^{11}$ or $S(O_2)R^{11}$, wherein $R^{11}$ is chosen from H, $C_1$–$C_{18}$-alkyl, $C_2$–$C_{18}$-alkenyl or $C_2$–$C_{18}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical in which a C atom in the ring is replaced by S, O or N; alkylaryl or alkylheteroaryl, saturated or unsaturated and mono- or polysubstituted or unsubstituted; aryl or heteroaryl, in each case mono- or polysubstituted or unsubstituted;

or $NR^{12}R^{13}$, $C(O)NR^{12}R^{13}$ or $S(O_2)NR^{12}R^{13}$, wherein $R^{12}$ and $R^{13}$ independently of one another are chosen from H, $C_1$–$C_{18}$-alkyl, $C_2$–$C_{18}$-alkenyl or $C_2$–$C_{18}$-alkinyl, in each case branched or unbranched and mono- or polysubstituted or unsubstituted; $C_3$–$C_7$-cycloalkyl, saturated or unsaturated and mono- or polysubstituted or unsubstituted, or a corresponding heterocyclic radical in which a C atom in the ring is replaced by S, O or N; alkylaryl or alkylheteroaryl, saturated or unsaturated and mono- or polysubstituted or unsubstituted; aryl or heteroaryl, in each case mono- or polysubstituted or unsubstituted;

or $R^{12}$ and $R^{13}$ together form a $C_3$–$C_7$-cycloalkyl, saturated or unsaturated and mono- or polysubstituted or unsubstituted, or a corresponding heterocyclic radical in which a C atom in the ring is replaced by S, O or N;

or $R^1$ and $R^2$ together form —CH=CH—CH=CH—, wherein the naphthyl system formed can be mono- or polysubstituted.

17. The process according to claim 1, characterized in that $R^1$=$R^{10}$, wherein $R^{10}$ is chosen from H, F, Cl, Br, I, $CF_3$, $NO_2$, $NH_2$; $C_1$–$C_4$-alkyl or $C_2$–$C_4$-alkenyl, branched or unbranched and mono- or polysubstituted or unsubstituted; $OR^{11}$, $C(O)OR^{11}$ or $SR^{11}$, wherein $R^{11}$ is chosen from H; $C_1$–$C_4$-alkyl, branched or unbranched and mono- or polysubstituted or unsubstituted; preferably H, $CF_3$ or $CH_3$, or $S(O_2)NR^{12}R^{13}$, wherein $R^{12}$ and $R^{13}$ independently of one another are chosen from H; $C_1$–$C_4$-alkyl, branched or unbranched and mono- or polysubstituted or unsubstituted.

18. The process according to claims 1, characterized in that $R^2$=$R^{10}$, wherein $R^{10}$ is chosen from H, F, Cl, Br, I, $SCH_3$; $C_1$–$C_4$-alkyl, $C_2$–$C_4$-alkenyl, branched or unbranched and mono- or polysubstituted or unsubstituted, preferably $CF_3$; $OR^{11}$, where $R^{11}$ is chosen from $C_1$–$C_4$-alkyl, branched or unbranched and mono- or polysubstituted or unsubstituted, preferably $CH_3$.

19. The process according to claim 1, characterized in that X is chosen from

H, F, Cl, OH, $CF_3$, O—$S(O_2)$—$C_6H_4$-$pCH_3$ or $OC(O)R^{12}$ where $R^{12}$=H; $C_1$–$C_4$-alkyl or $C_2$–$C_4$-alkenyl, branched or unbranched and mono- or polysubstituted or unsubstituted, preferably H, F, Cl, OH, O—$S(O_2)$—$C_6H_4$-$pCH_3$, $OC(O)R^{12}$ where $R^{12}$=$C_1$–$C_4$-alkyl, preferably $CH_3$.

20. The process according to claim 4, wherein the enzyme used is a pig liver esterase.

21. The process according to claim 5, wherein the solvent is an aqueous buffer system, with a pH of between 6.0 and 8.0.

22. The process according to claim 7, wherein the organic solvent is acetone or butanol.

23. The process according to claim 7, characterized in that at least one organic solvent is added to the aqueous buffer system up a percentage content by volume of between 5 and 20%.

24. The process according to claim 9, wherein the bases include potassium tert-butylate or sodium hyride.

25. The process according to claim 9, wherein the solvent is tetrahydrofuran or dimethylformamide.

26. The process according to claim 13, wherein the lipase is a lipase from *Candida rugosa, Candida cylindracea* or *Pseudomonas cepacia*.

27. The process according to claim 14, wherein the organic solvent is toluene.

28. The process according to claim 17, wherein $R^1$ is chosen from H, F, Cl, OH, $CH_3$, $C_2H_5$, $C_2H_3$, $CF_3$, $SCH_3$, $OCF_3$, $OCH_3$, $OC_2H_5$, $C(O)OCH_3$, $C(O)OC_2H_5$.

29. The process according to claim 17, wherein $R^1$ is m-$OCH_3$.

30. The process according to claim 18, wherein $R^2$ is H.

31. The process according to claim 19, wherein X is OH, F or Cl.

* * * * *